United States Patent
Sotereanos et al.

(10) Patent No.: US 9,877,861 B2
(45) Date of Patent: Jan. 30, 2018

(54) SHOULDER AND ARM ORTHOSIS

(75) Inventors: Dean G. Sotereanos, Allison Park, PA (US); Darrell Seretti, Pittsburgh, PA (US); James Grant, Sewickley, PA (US); Joshua Cordle, Moon Township, PA (US); Leslie Seretti, legal representative, Pittsburgh, PA (US)

(73) Assignee: Elizur Corporation, Pittsburgh, PA (US)

( * ) Notice: Subject to any disclaimer, the term of this patent is extended or adjusted under 35 U.S.C. 154(b) by 1320 days.

(21) Appl. No.: 13/158,248

(22) Filed: Jun. 10, 2011

(65) Prior Publication Data

US 2012/0010546 A1 Jan. 12, 2012

Related U.S. Application Data

(60) Provisional application No. 61/397,451, filed on Jun. 11, 2010.

(51) Int. Cl.
*A61F 5/00* (2006.01)
*A61F 5/01* (2006.01)

(52) U.S. Cl.
CPC .................................. *A61F 5/0118* (2013.01)

(58) Field of Classification Search
CPC .......... A61F 5/01; A61F 5/0118; A61F 5/013; A61F 5/3723
USPC .................... 602/4, 5, 20; 128/845, 877–881
See application file for complete search history.

(56) References Cited

U.S. PATENT DOCUMENTS

| 4,214,579 | A | * | 7/1980 | Ford | 602/4 |
| 5,334,132 | A | * | 8/1994 | Burkhead | 602/4 |
| 5,464,383 | A | | 11/1995 | Padden et al. | |
| 5,665,058 | A | | 9/1997 | Young | |
| 7,244,239 | B2 | | 7/2007 | Howard | |
| 7,300,410 | B1 | | 11/2007 | Weber | |
| 7,563,236 | B2 | | 7/2009 | Kazmierczak | |
| 2006/0258966 | A1 | * | 11/2006 | Hargrave et al. | 602/20 |
| 2008/0019770 | A1 | | 5/2008 | Miller | |
| 2008/0119770 | A1 | * | 5/2008 | Miller | 602/4 |

OTHER PUBLICATIONS

International Search Report, PCT/US2011/040072, ISA/US, dated Nov. 15, 2011, 2 pages.

* cited by examiner

*Primary Examiner* — Ophelia A Hawthorne
*Assistant Examiner* — Caitlin Carreiro
(74) *Attorney, Agent, or Firm* — The Webb Law Firm

(57) ABSTRACT

A shoulder and arm orthosis assembly for supporting at least one of a shoulder, arm, wrist and hand of a user. The orthosis assembly provides a sling with a shoulder strap, a wrist/hand orthosis, and a pillow support to hold the arm of the user away from the body. The sling has attached inner and outer portions that are configured to be detached and reattached with one another. The wrist/hand orthosis may be supported by the sling when the sling is closed and may be permitted to exit the sling when the sling is opened.

15 Claims, 11 Drawing Sheets

SHOULDER AND ARM ORTHOSIS

CROSS REFERENCE TO RELATED APPLICATION

This application claims the benefit of priority of U.S. Provisional Patent Application Ser. No. 61/397,451, filed Jun. 11, 2010, on which this patent application is based and which is incorporated herein by reference in its entirety.

FIELD OF THE DISCLOSURE

The present disclosure generally relates to orthotic devices and methods for assisting in the support of limbs and joints of users and, more particularly, to a shoulder and arm orthosis having a sling with a bottom opening and a pivotable support to allow for flexing and extension of a user's elbow without removing the orthosis from the shoulder and/or portions of the arm.

BACKGROUND

The present disclosure is concerned with conditions and care of the shoulder and elbow which, whatever the primary method of treatment, may be managed post-operatively following a shoulder injury or non-operatively as part of a treatment plan, mainly by immobilization of the shoulder in a selected position, but where, in some cases or at some stages, an option for early mobilization of the forearm/elbow would be useful.

In most cases, users having shoulder surgery wear a sling post-operatively to stabilize the shoulder. Typically, surgeons recommend that the sling be worn at all times, even when the user is sleeping. Alternatively, slings also may be recommended by doctors as part of a non-operative shoulder/elbow treatment plan.

The traditional sling has a square or rectangular section of cloth that is folded to form a pocket for supporting a user's arm, thereby providing immobilization to the injured shoulder. The folded cloth is suspended from the user's neck and/or shoulders to retain the limb/arm in a fixed position. While the immobilization that the sling provides may result in some healing, it may also have a debilitating effect on the shoulder and/or elbow joints and muscles causing stiffness and loss of extension range. For example, in case of a shoulder sling, extended immobilization of the elbow may result in cubital tunnel syndrome. Some research indicates that in 10-20% of shoulder surgeries or non-operative treatments requiring shoulder slings, cubital tunnel syndrome will emerge and will require intensive physical therapy or additional surgery to cure it. Hence, when a user wears a shoulder sling, physicians often will instruct the user to periodically take the sling off, and flex and extend the elbow repeatedly to prevent cubital tunnel syndrome. However, there are several significant risks when the user takes the sling off, including injury to the user's shoulder (which itself may be in need of recovery) that is no longer supported by the sling.

Hence, it is desirable to devise a shoulder and arm orthosis that addresses the need to support the shoulder and arm and prevent cubital tunnel syndrome, yet provides a mechanism to securely and comfortably flex and extend the elbow without requiring the user to remove the supporting orthosis. This orthosis may desirably allow the user to easily disengage the forearm to flex and straighten out the elbow without requiring removal. It is further desirable to provide a shoulder and arm orthosis that allows for rehabilitative training of the user's arm and/or shoulder for physical therapy while allowing the user's arm and/or shoulder to remain supported by the orthosis. The shoulder and arm orthosis may also desirably provide support for portions of the arm, including the wrist/hand, when needed.

SUMMARY OF INVENTION

Therefore, it is an object of the present invention to provide a shoulder and arm orthosis that overcomes some or all of the known drawbacks and deficiencies.

A shoulder and arm orthosis according to the teachings of the present disclosure addresses the need to support the shoulder and portions of the arm to assist in preventing cubital tunnel syndrome by allowing flexing and extension of the elbow without the need to remove the orthosis. Furthermore, the orthosis may be configured to provide support for the user's elbow, wrist, and hand with a pivotable support and telescoping wrist/hand orthosis (WHO).

In one embodiment, the present disclosure relates to an orthosis assembly for supporting at least one of a shoulder, arm, wrist and hand of a user comprising a sling, a wrist/hand orthosis supported by the sling, and a shoulder strap. The sling has attached inner and outer portions, wherein the inner and outer portions are configured to be detached and reattached.

In one embodiment, the present disclosure relates to an orthosis for supporting at least one of an arm, wrist and hand of a user. The orthosis includes a first member attachable to a sling, a second member in pivotal communication with the first member, a first strap positioned about a portion of the second member and configured to support the arm of the user, a second strap positioned about a portion of the second member near the end of the second member and configured to support at least the wrist of the user, and a grip positioned at an end of the second member for supporting the hand.

In one embodiment, the present disclosure relates to a kit for a shoulder and arm orthosis having a sling configured allow opening of said sling near its bottom, a wrist/hand orthosis supported by the sling, a strap connected to the sling and configured to support same, and a support configured to maintain the sling in a desired position.

In one embodiment, the present disclosure relates to a method to control flexion or extension of the elbow joint using a pivotable support integrated in a shoulder and arm orthosis. The method includes positioning a strap of a sling of the shoulder and arm orthosis about a neck of a user, positioning an arm, wrist and hand of a user into a wrist/arm orthosis positioned within the sling, and securing the arm, wrist and hand of the user to said wrist/arm orthosis.

These and other features and characteristics of the present invention, as well as the methods of operation and functions of the related elements of structures and combinations of parts and economies of manufacture, will become more apparent upon consideration of the following description and the appended claims with reference to the accompanying drawings, all of which form a part of this specification, wherein like reference numerals designate corresponding parts in the various figs. It is to be expressly understood, however, that the drawings are for the purpose of illustration and description only and are not intended to unduly limit the present invention. As used in the specification and the claims, the singular form of "a", "an", and "the" include plural referents unless the context clearly dictates otherwise.

DETAILED DESCRIPTION

Figure 1:
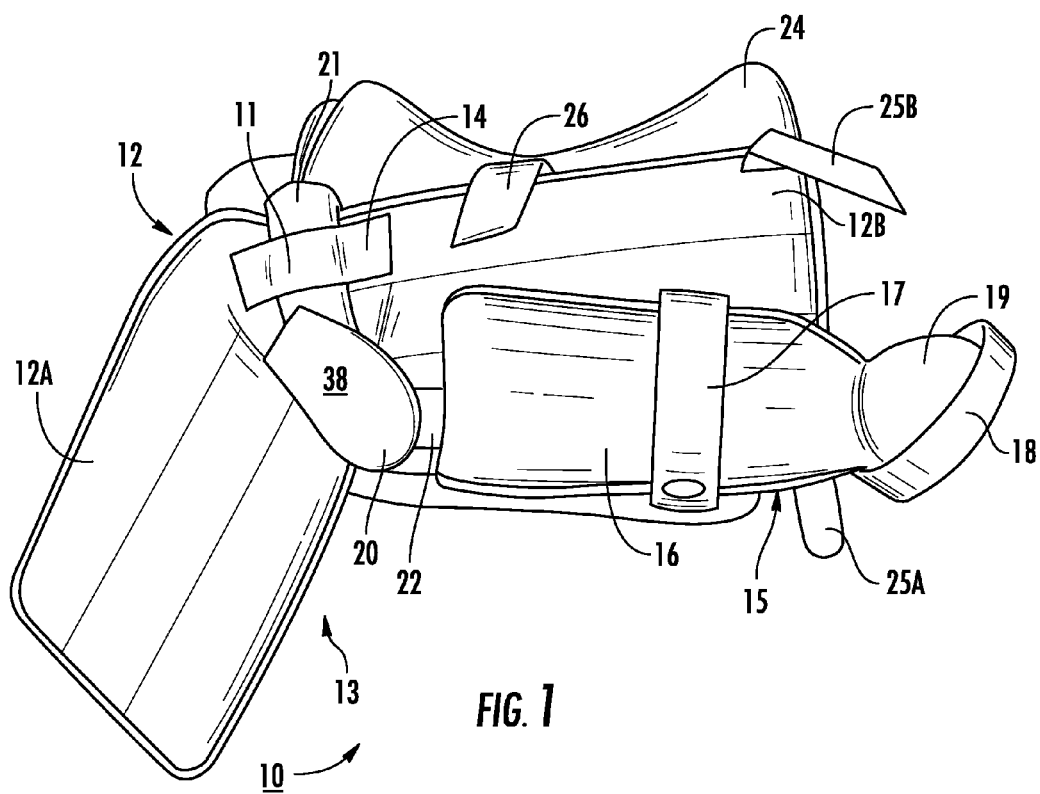
FIG. 1 is a side view of an embodiment of an orthosis in accordance with the present invention.

For purposes of the description hereinafter, the terms "upper", "lower", "right", "left", "vertical", "horizontal", "top", "bottom", "lateral", "longitudinal" and related derivatives thereof shall relate to the invention as it is oriented in the drawings. However, it is to be understood that the present invention may assume various alternative variations, except where expressly specified to the contrary. It is also to be understood that the specific devices and configurations illustrated in the attached drawings, and described in the following specification, are simply exemplary embodiments of the invention. Hence, specific dimensions and other physical characteristics related to the embodiments disclosed herein are not to be considered as unduly limiting.

It is noted here that various figures shown and discussed herein are for illustrative purpose only, and are not drawn to scale. The figures facilitate discussion of a shoulder and arm orthosis configuration according to one or more embodiments of the present disclosure without necessarily limiting the orthosis configuration to the dimensions, designs, or illustrations depicted therein.

FIG. 1 illustrates an embodiment of a shoulder and arm orthosis assembly 10 according to the present disclosure. In one embodiment, the orthosis assembly 10 may include a shoulder sling 12 having outer and inner portions 12A and 12B, respectively, a Wrist/Hand Orthosis (WHO) 15, a pivotable support 20, and an abduction pillow 24. The sling 12 may be made of durable cloth or other suitable fabrics. The bottom end 13 of the sling 12 can be fully opened (as discussed later hereinbelow) to substantially separate the bottom of outer and inner portions 12A, 12B of the sling 12 and may allow a user's elbow to be extended (as shown, for example, in FIG. 5 fully extended and discussed later hereinbelow) without the need to remove or take off the sling 12 from its neck attachment. Plastic boning material (not shown) may act as support stays and line both sides of the bottom 13 of the sling 12 to keep the bottom 13 semi-rigid and make it easier to close.

In one embodiment, the orthosis assembly 10 may internally include an insertion strap 14 to support attachment of the WHO 15 inside the sling 12 via the pivotable support 20. The WHO 15 thus can be made an integral part of the sling 12 while also being removed from the orthosis assembly 10. The strap 14 may be positioned linking portions 12A-12B of the sling 12 as shown by way of example in FIG. 1. Alternatively, the strap 14 may support the sling 12 by attaching only to the inner portion 12B. The WHO 15 may be designed to provide support from the wrist of the user to the end of the user's hand 30 (as shown, for example, in FIG. 3). In one embodiment, the WHO 15 may be made of a concave member 16 to support a user's forearm using a strap 17. A wrist strap 18 also may be provided as part of the WHO 15 for additional support. The concave member 16 may be constructed of metal or plastic with fabric 42 on top or other suitable material (e.g. see FIG. 9) to support the forearm of the user. The layer of fabric 42 may line the "top" or user side of the concave member 16 of the WHO 15 to provide a softer, comfortable surface against the skin of user's arm. Additional "openings" 44 also may be provided on the concave member 16 to provide for improved airflow and afford "breathability" to the fabric layer 42.

A semi-rigid hand grip 19 may be provided at the end of the WHO 15 and may be constructed of cloth or other materials suitable for grasping by the user's hand 30. The grip 19 may further be attached to the concave member 16 and be compressible for strength-training and flexing of user's fingers and wrist, and also to provide grip for the user's fingers (as shown, for example, in FIGS. 2-3).

The pivotable support 20, as shown in the illustrated figures, includes a hinge mechanism in one preferred embodiment, although other mechanisms may be used to provide pivotable support. The pivotable support 20 may use upper and lower stays 21 and 22, respectively, made of metal and/or plastic to support the WHO 15 to the pivotable support 20 and/or sling 12, so as to enable flexible engagement of the WHO 15 with the sling 12. Although stays 21, 22 may be composed of metal and/or plastic, other suitable materials or combinations thereof may be employed in accordance with the present invention.

Figure 8:
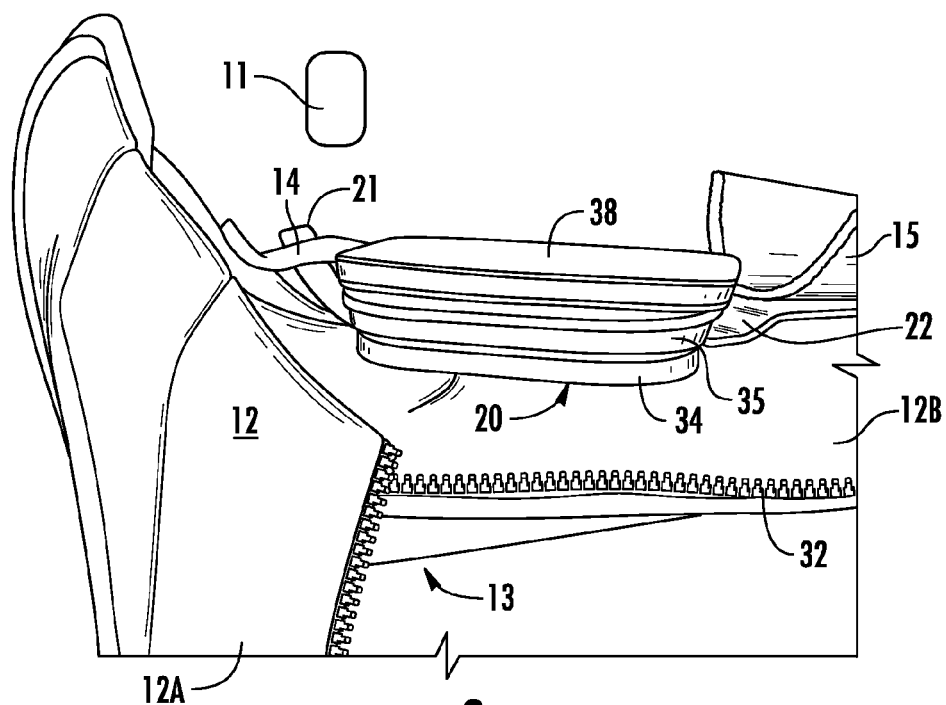
FIG. 8 is a side view of and embodiment of a pivotable support of the orthosis shown in FIG. 6 in accordance with the present invention.
Figure 11:
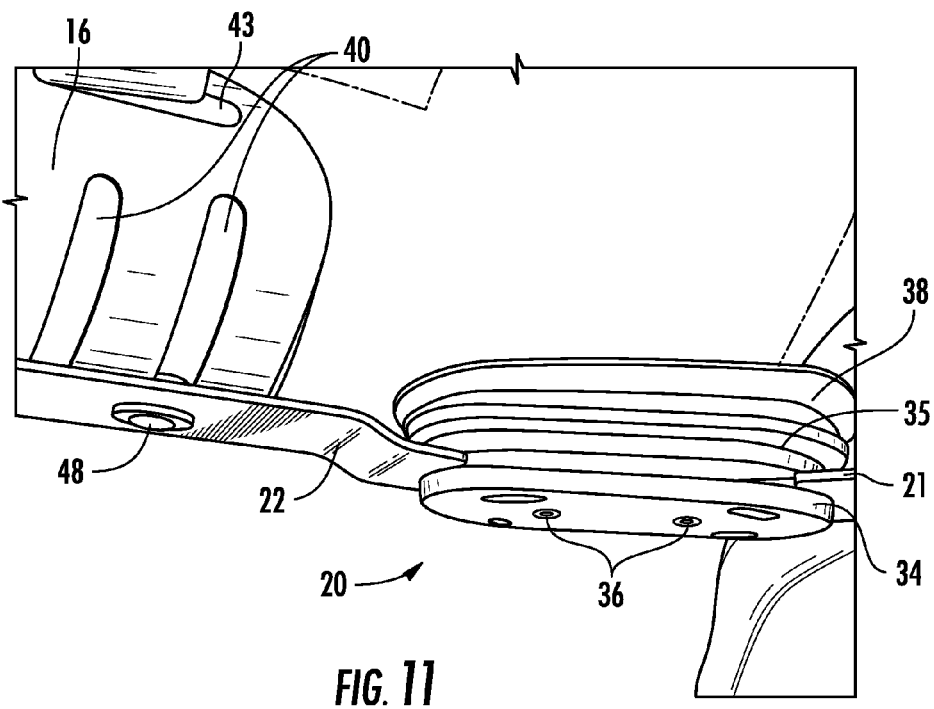
FIG. 11 is a partial perspective view of the orthosis shown in FIG. 9 in accordance with the present invention.
Figure 12:
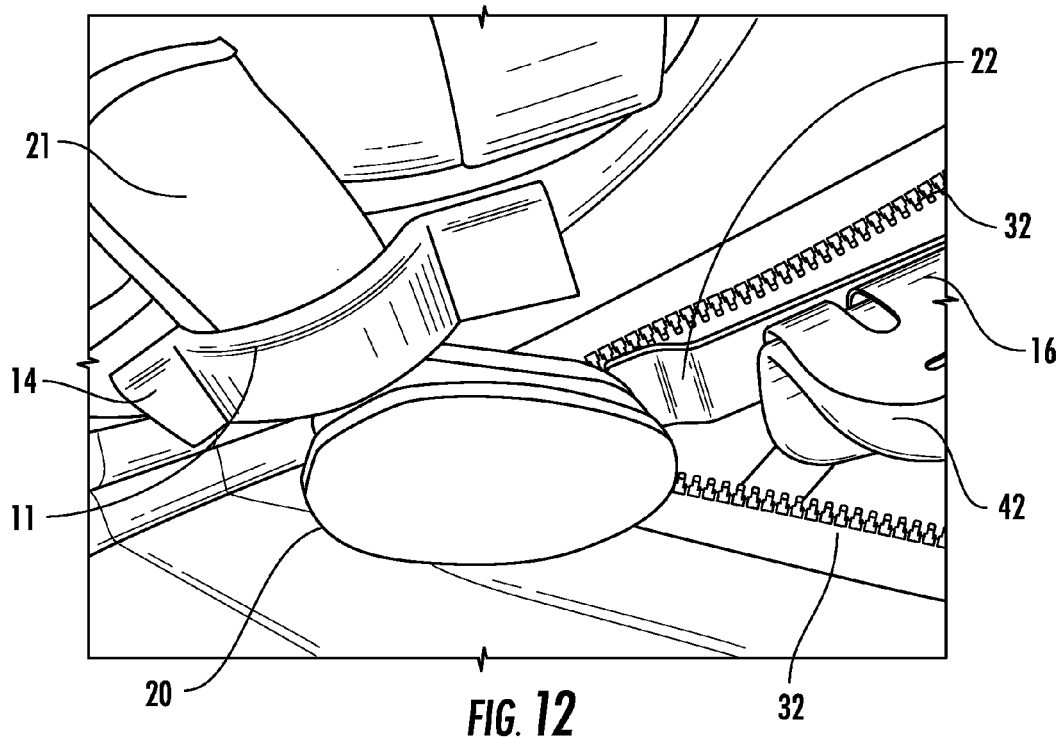
FIG. 12 is a partial perspective view of the orthosis shown in FIG. 9 in accordance with the present invention.

As can be seen in FIGS. 1, 11, 12, upper stay 21 may be attached to the pivotable support 20 and inserted into the strap 14 to support placement of the pivotable support 20 inside the sling 12. In one embodiment, the insertion strap 14 may use Velcro™ or other suitable fastening material on its interior surface—i.e., the surface that is in contact with the stay 21. In that case, the upper stay 21 may be covered with suitable fabric for providing secure engagement of the pivotable support 20 inside the sling 12 when the fabric comes in contact with the fastening material on the interior surface of the strap 14. Alternatively, or in addition to, the upper stay 21 may have Velcro™ affixed to the inside of the upper stay 21 so as to directly engage the inner portion 12B for supporting the pivotable support 20. The stay 21 may also avoid exposing metallic or plastic surfaces against a user's skin inside the sling 12 via padding 11 shown in FIGS. 1 and 12. Such padding 11 may be incorporated into the strap 14 as illustrated or alternatively be separable and attachable to upper stay 21 and/or strap 14 as shown in FIG. 8. Padding 11 may comprise compressible materials for comfort such as, for example, cotton, foam, memory foam, etc.

In one embodiment, the upper stay 21 may be connected to the pivotable support 20 via a nut-bolt mechanism or other suitable fastening mechanism that may provide a firm (non-movable) connection to the pivotable support 20 as will be discussed further hereinbelow with regards to FIG. 11. In one embodiment, the lower stay 22, connecting the WHO 15 to the pivotable support 20, may be pivoted and may further be rotated about its longitudinal axis while fastened to the pivotable support 20 using, for example, a rivet-type mechanism 48 and slots 40, as will discussed further hereinbelow with regards to FIGS. 9-11 and 13. It is noted here that the entire pivotable support and WHO assembly 15 may be easily removed from the sling 12, if so desired, via release of rivet-type mechanism 48 from slots 40. Hence, the WHO 15 may be angularly moved by the user under the rotational control by the pivotable support 20.

Furthermore, to control flexion and extension of a user's elbow, one or more stays 21, 22 may be connected to a series of tabs so as to place limits on the movement of the user's forearm. Accordingly, the inner and outer hinge members 34, may further sandwich a series of tabs (not shown) to provide controlled flexion of a user's forearm, thereby avoiding abrupt or uncontrolled straightening of the arm by the user and thus preventing additional injury to the recovering shoulder tissues. In other words, these tabs may allow controlled flexion/extension of the user's elbow in a gradual (or tabbed) manner. In addition, other modes of motion may be supported and/or controlled relating to, for example, the bicep, tricep, forearm, etc.

As can be seen in FIGS. 2-9, 14-15, in one embodiment, the orthosis assembly 10 also may include pillow 24 for abduction at various desired angles, such as, for example, 90 or 65 degrees. The pillow 24 may be attached to the orthosis assembly 10 with Velcro™ or other suitable fastener (e.g., buttons) or fastening material. In one position, the pillow 24 may support the arm in the sling 12 at about 90 degrees of abduction, whereas flipping the pillow 24 in another position would support the arm at about 65 degrees of abduction with the sling 12 attached.

A waist band 28 is shown, for example, in FIGS. 2-3 and 14-15, and may be provided separately or sewn as part of the pillow 24 to allow steady positioning of the pillow 24 against a user's waist. In an alternative embodiment, a second pillow (not shown) providing abduction at other desired angles such as, for example, 40 and 25 degrees, also may be provided as part of the orthosis assembly 10. On the other hand, in one embodiment, another pillow with three sides providing abduction at three desired angles such as, for example, 90 degrees, 45, degrees, and 20 degrees, respectively, may be provided instead of two separate pillows. In another embodiment, the first pillow may provide abduction at 90 degrees, whereas the second pillow may provide abduction at 40 and 20 degrees. Hence, support for a number of different abduction angles desired may be provided with suitable combination of one or more of such pillows, or design of other pillows with desired angles of abduction.

Referring again to FIG. 1, in one embodiment, the sling 12 may also include additional tabs/straps 25A, 25B, 26 for providing fastening means for the outer and inner sides of the sling 12A, 12B. It is observed here that although the orthosis 10 may be opened and closed from the bottom 13, tabs 25A, 25B at the wrist end of the sling 12 may keep the orthosis 10 together as the sling 12 is opened and closed from the bottom 13. Further, tabs 25A and 25B may serve to support the forearm when fastened. In one embodiment, the tab 25A may be provided on the outer layer of the inner portion 12B and the tab 25B may be provided on the inside layer of the inner portion 12B (as shown, for example, in FIGS. 6-7). The tabs 25A, 25B may use Velcro™ or other fastening means (e.g., buttons) to keep the wrist end of the inner portion 12B together as the sling 12 is opened from the bottom 13. In addition to tabs 25A, 25B, another strap 26 may be provided on the outer layer of inner portion 12B and may be fastened against the outer layer of the sling outer portion 12A with Velcro™ or other suitable adhesive material to provide overall closure of the sling 12 as illustrated, for example, in FIG. 2.

Figure 2:
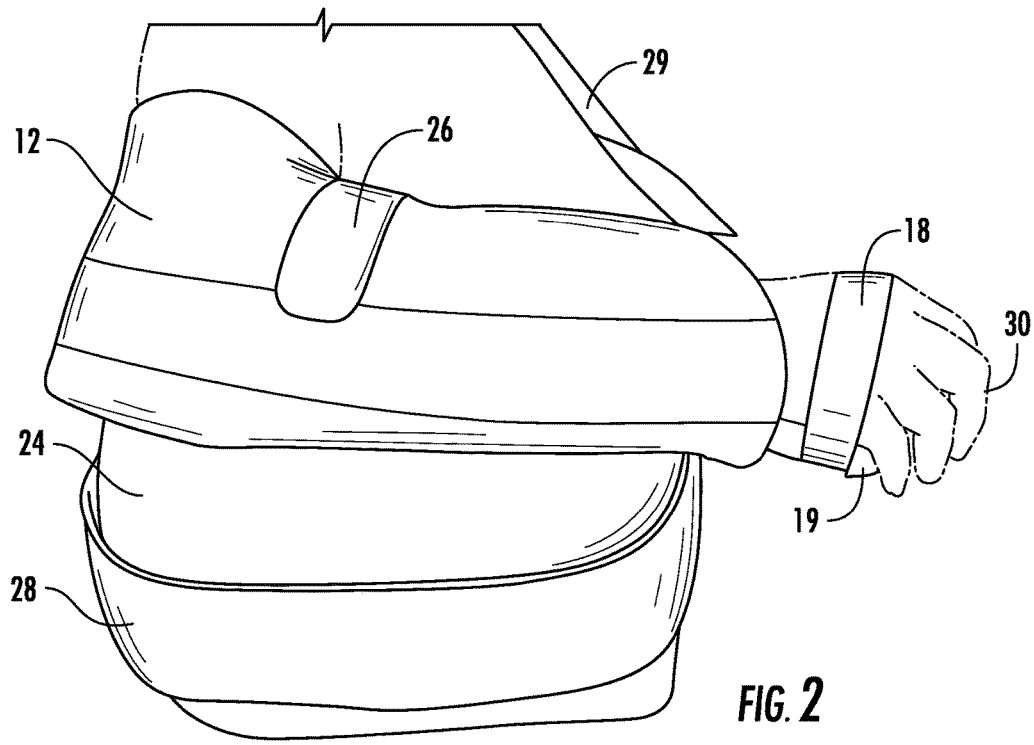
FIG. 2 is a side view of an embodiment of an orthosis as it may be employed by a user in accordance with the present invention.

FIG. 2 illustrates an exemplary side view of the sling 12 with user's arm in abduction against the pillow 24. As mentioned before, the abduction pillow 24 may be positioned against the waist of the user and tied around the waist using the waist band 28 as illustrated, for example, in FIGS. 14-15. The sling 12 may be closed with the strap 26, while maintaining the user's forearm/hand 30 inside the WHO 15 (not visible in FIG. 2). The ball 19 at the end of the WHO 15 may provide the grip to user's fingers and provide means to strengthen the fingers. The sling 12 may be worn by the user and held in place by a neck strap 29 (shown partially in FIG. 2, and in relatively more detail in FIG. 14).

Figure 3:
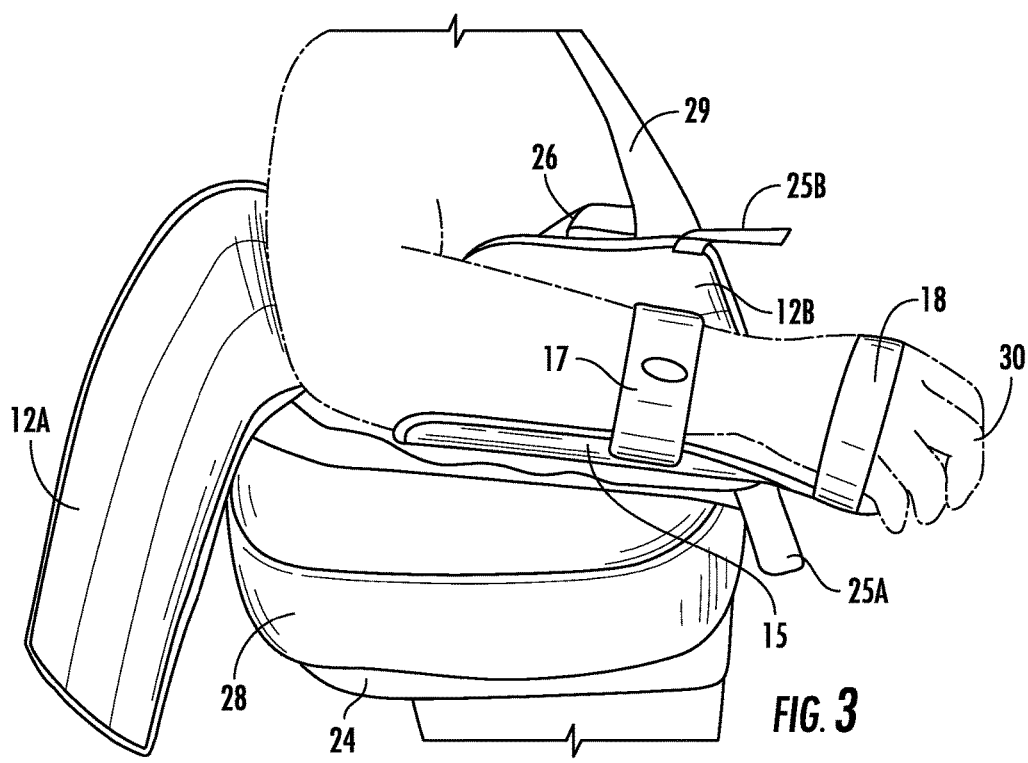
FIG. 3 is a side view of the orthosis shown in FIG. 2 in an opened orientation as may be employed by a user in accordance with the present invention.

FIG. 3 shows an additional exemplary side view of the sling 12 in FIG. 2, with the sling 12 in an opened orientation and the user's arm in abduction and affixed in the WHO 15. The pillow 24 is secured around the user's waist and is supporting the underside of the forearm and elbow of the user. Accordingly, the user is now enabled to reposition their forearm now that outer internal layer 12A has been detached from at least one adjacency with inner internal layer 12B. Various parts of the orthosis assembly 10 in FIG. 3 are already discussed hereinbefore and, hence, additional discussion of the same is not repeated herein for the sake of brevity.

Figure 4:
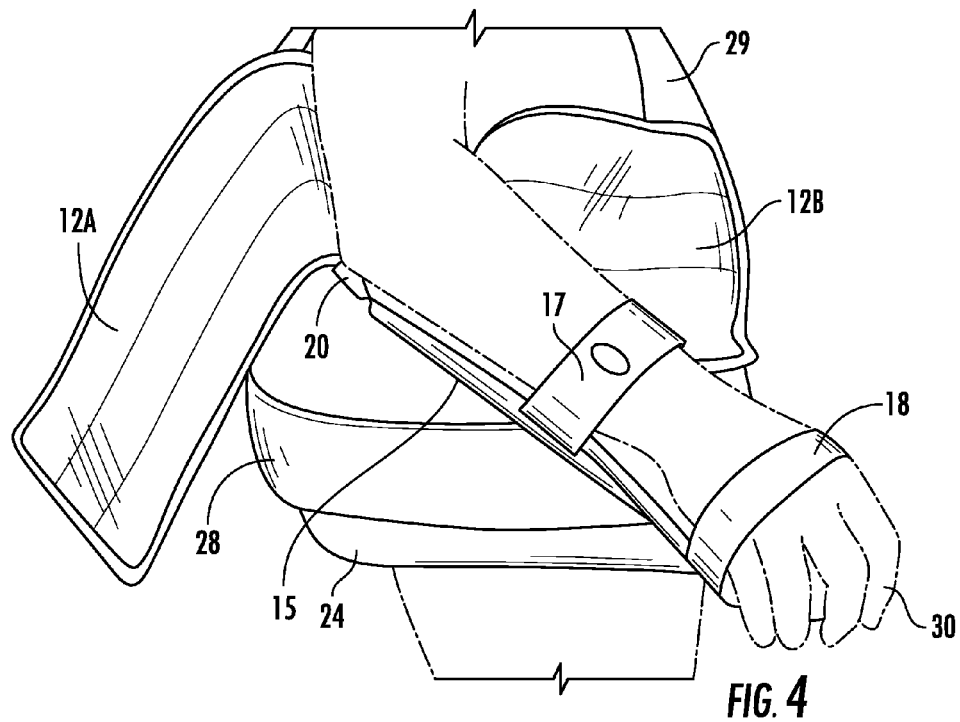
FIG. 4 is a side view of the orthosis shown in FIG. 3 as it may be employed by a user repositioning their elbow in accordance with the present invention.
Figure 5:
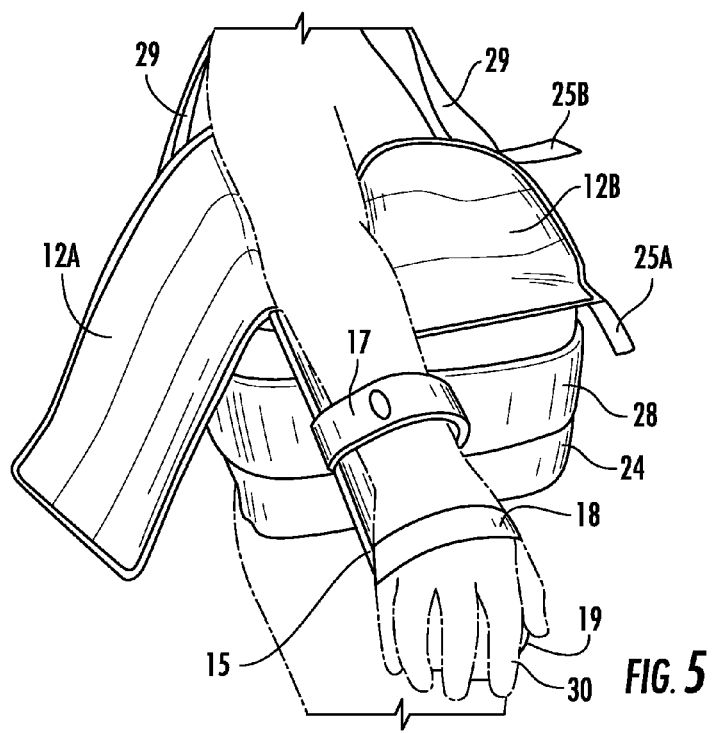
FIG. 5 is a side view of the orthosis shown in FIG. 3 as it may be employed by a user repositioning their elbow in accordance with the present invention.

FIGS. 4 and 5 illustrate how a user's forearm in abduction can be fully extended out of the sling 12 according to one embodiment of the present disclosure. It is noted here that shoulder joint movements include flexion, extension, abduction, adduction, and internal and external rotation. The support for the elbow, wrist, and hand can be provided with the pivotable support 20 and the telescoping WHO 15. The pivotable support 20 as seen in FIG. 4, for example, at the elbow may control flexion and extension of the shoulder through a series of tabs to place limits on the movement of the user's shoulder joints. In addition, as mentioned before, the WHO 15 can be flexibly and/or rotatably positioned against the user's forearm to adjust internal and external axial rotation of the WHO 15, and hence, the rotation of the shoulder joints connected to the forearm in the WHO 15. The combination of the pivotable support 20 and the pillow 24 may provide abduction and adduction support for the shoulder joints.

It is observed here that because of the sling's 12 ability to be fully opened without removing the neck strap 29 or the sling 12 from the user's body, the user can freely flex and extend the elbow while still retaining the support of the orthosis assembly 10 for the shoulder using the neck strap 29 around the neck of the user and forearm in abduction. Hence, user's flexing of his/her elbow is provided not at the expense of removing the sling support for the recovering shoulder. Thus, the openable sling 12 according to the teachings of the present disclosure addresses the need to support the shoulder and prevent cubital tunnel syndrome, yet provides for a mechanism to comfortably flex and extend the elbow without requiring the user to take off the sling 12.

As is shown in FIGS. 4 and 5, the opening of the bottom 13 of the sling 12 allows the user to easily disengage the forearm from the sling 12 to flex and straighten out the elbow without requiring the removal or adjustment of the entire orthosis assembly 10. However, the user may choose to retain support of the WHO 15 by keeping wrist strap 18 and forearm strap 17 affixed along with grasping the grip 19 while repositioning the elbow as shown. Accordingly, the lower arm of the user is supported by the WHO 15, which is supported by the sling 12.

Figure 6:
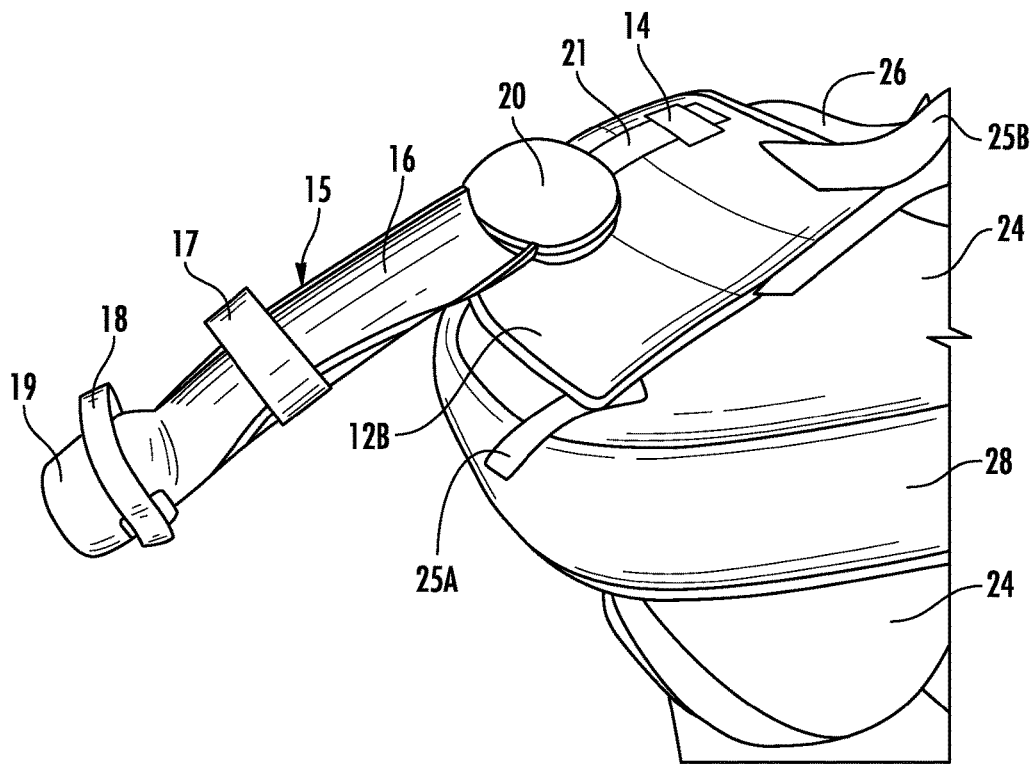
FIG. 6 is a perspective view of an embodiment of an orthosis in accordance with the present invention.
Figure 7:
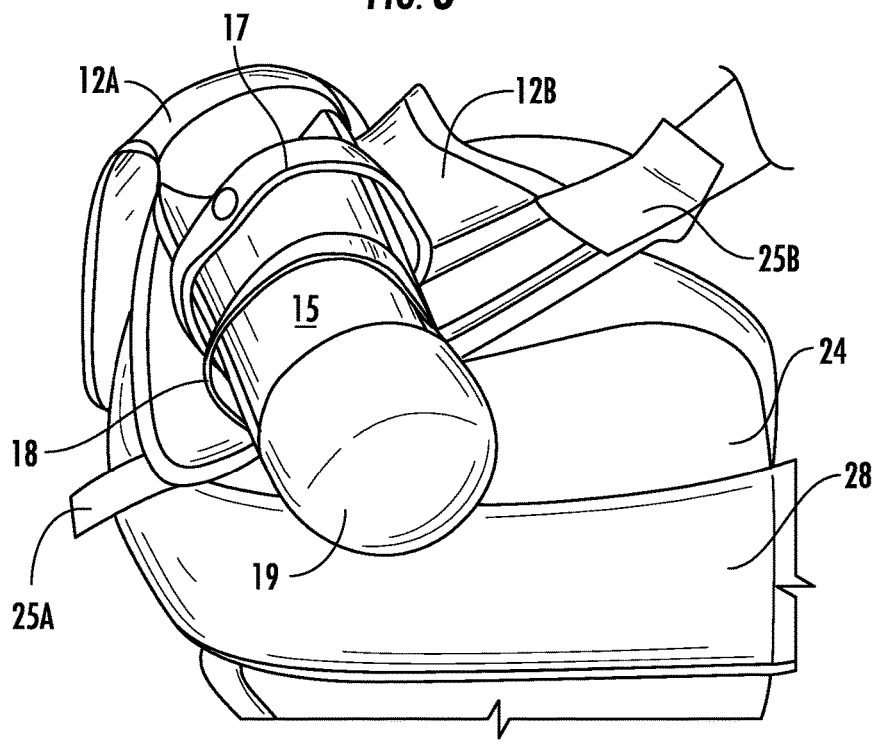
FIG. 7 is a perspective view of an embodiment of an orthosis in accordance with the present invention.

FIG. 6 is an exemplary front perspective view of the orthosis assembly 10 corresponding to the orthosis assembly 10 in FIG. 5 viewed from the right-hand side of the user's fully-extended arm. In FIG. 6, the orientation of only the component parts of the orthosis assembly 10 is shown without depicting the user's arm. The orientation of the pivotable support 20 and WHO 15 (when the arm is in the extended position of FIG. 5) is more clearly visible in FIG. 6. Similarly, FIG. 7 shows another exemplary front perspective view of the orientation of various components of the orthosis assembly 10 in FIG. 5. The front view of FIG. 7 corresponds to the view of the orthosis assembly 10 configuration in FIG. 5 obtained when the viewer faces the fully-extended arm. Various components of the orthosis assembly 10 configuration in FIGS. 6 and 7 are already discussed hereinbefore and, hence, additional discussion of the same is not repeated herein for the sake of brevity.

As illustrated in FIGS. 2-5, 8-9, the sling 12 may be a somewhat of traditional sling with an openable closure at the bottom 13. The opening may be such that the sling 12 may be fully opened from the bottom 13 starting from the wrist end of the orthosis assembly 10 and ending near the user's elbow. Thus, the opening may extend all the way to the end of the orthosis assembly 10 and allows the user's hand 30 to easily fit into the WHO 15.

FIG. 8 depicts an exemplary close-up view of the pivotable support 20 inside the sling 12, as well as a zipper 32 on the sling 12 functioning as an opening/closing means in one embodiment of the present disclosure. The sling 12 may be thus closed and opened with a large zipper 32 and a tab (not shown) placed on the end of the zipper 32 to make it easier for the user to reach the zipper with the unaffected arm. It is noted here that, in various embodiments, other openings/closing means may be employed including, but not limited to, buttons, snaps, magnets, Velcro™, clips, interlinking tabs, sealing arrangements, etc. Accordingly, because of the zipper 32 or other opening/closing means is in an opened orientation, while the WHO 15 is secured to the user's forearm, the elbow may be repositioned safely by the user without removing the sling 12. The zipper 32 can be opened to let the wrist and hand 30 of the user come out of the sling 12 while securing the elbow on the pivotable support 20. As mentioned before, the Velcro™ tabs 25A, 25B at the wrist end of the sling 12 may provide support as it is zipped open and shut. Thus, the wrist and hand 30 of the user can drop out of the orthosis assembly 10 and be supported by the WHO 15 (with tabbed friction from the pivotable support 20) and the tabs 25A, 25B.

Furthermore, plastic boning material (or plastic stays) may line bottoms of both portions 12A, 12B of the sling 12 to keep those bottoms semi-rigid and thereby making them easier to close with the zipper 32. Thus, the zippered opening retains its form with these plastic stays integrated into the fabric of the orthosis assembly 10 to facilitate easy closure by the user.

FIGS. 8 and 11 depict close-up views of the inner and outer hinge members 34, 35, respectively, having the upper and lower stays 21, 22, respectively linked thereto. More specifically, the inner and outer hinge members 34, 35, respectively, are substantially flat plates comprised of metal and/or plastic and cover end portions of upper and lower stays 34, 35 pivotally linking the upper stay 21 to the lower stay 22. Thus, the upper and lower stays 21, 22 may be sandwiched between the hinge members 34, 35 and connected to the same via retaining pins 36 positioned through the ends of upper and lower stays 21, 22 and secured to hinge members 34, 35 as illustrated in FIG. 11. As mentioned before, the pivotable support 20 may be positioned and secured inside the sling 12 by "inserting" the stay 21 inside the strap 14.

The inner and outer hinge members 34, 35 may further sandwich a series of tabs and/or a rotation retarding means (not shown) to provide controlled flexion of a user's forearm, thereby avoiding abrupt or uncontrolled straightening of the arm by the user and thus preventing additional injury to the recovering shoulder tissues. At least lower stay 22 (connecting the WHO 15 to the pivotable support 20) may be linked or attached to the tabs and or rotation retarding means placed between the hinge members 34, 35 so as to provide tabbed/controlled angular movement of the user's arm in the WHO 15.

The pivotable support 20 may also include a cloth-covered gel pad 38 as a top layer of the pivotable support 20 to prevent skin abrasion. The gel padding 38 may thus cover the pivotable support 20 for the user and may prevent lateral epicondylitis ("tennis elbow") in the user. Also shown in FIG. 8 is padding 11, which may be separable from the strap 14 as illustrated, and may also be configured to prevent skin abrasion.

FIGS. 9-13 depict additional constructional and attachment details for the WHO 15 according to one or more embodiments of the present disclosure. The concave member 16 may have one or more bolts with corresponding locking nuts (as illustrated, for example, in FIGS. 9-10 as slot engaging mechanism 48) to allow internal or external rotation of the WHO 15 to control pronation/supination of the user's forearm. For example, in case of internal rotation of the WHO 15, the WHO may be rotated by the user for proper arm adjustment and comfort even when the user's arm is in the WHO 15 and the WHO itself is inside the sling 12. Accordingly, concave member 16 of the WHO 15 may include one or more connection slots 40 to allow connection of the WHO 15 to the plastic or metallic stay 22 (and, hence, to the pivotable support 20) using slot engagement mechanism 48, shown in FIG. 10, for each such slot 40. The engagement of the stay 22 with the WHO 15 using slot engaging mechanism 48 provides for a slidable engagement—i.e., each nut and bolt pair may slide inside its corresponding slot 40 so as to allow for internal and external rotation of the WHO 15 to a predetermined extent, thereby controlling pronation/supination of the user's forearm.

Furthermore, the slots 40 may allow the concave member 16 to provide telescoping support for different lengths of users' arms. The lower stay 22 can be detached via slot engaging mechanisms 48 and connected to another appropriate slot 40 to "shorten" or "extend" the overall length of the WHO 15 supporting the user's arm. The number and placement of slots 40 can be selected as per design considerations.

Figure 9:
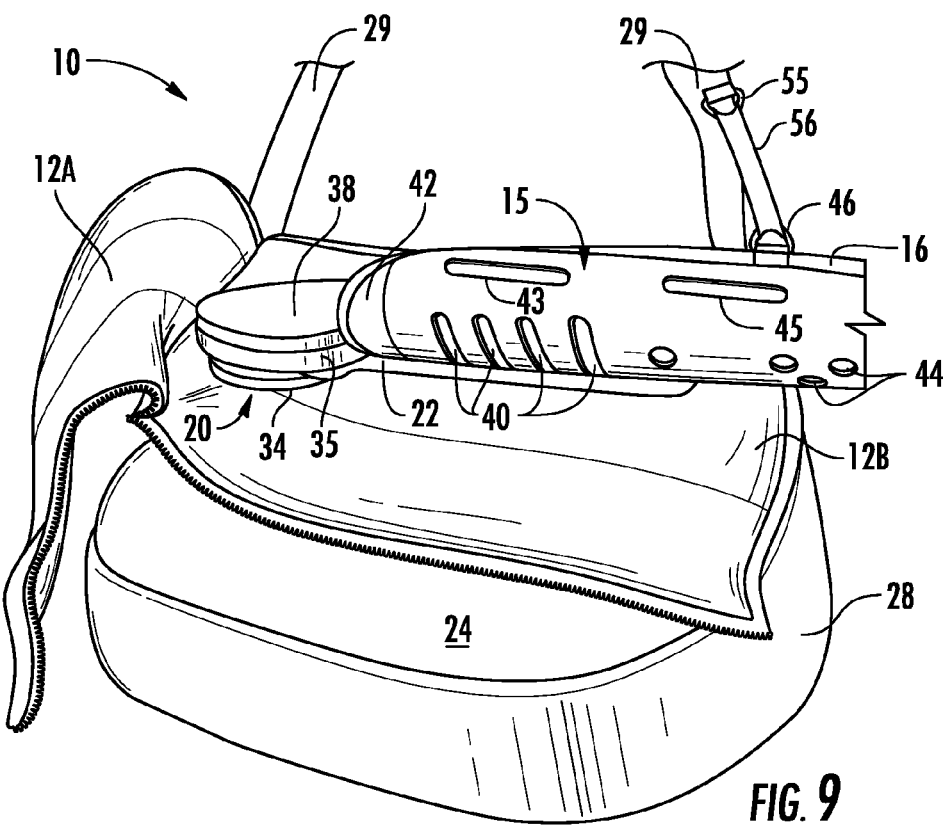
FIG. 9 is a side view of an embodiment of an orthosis in accordance with the present invention.
Figure 10:
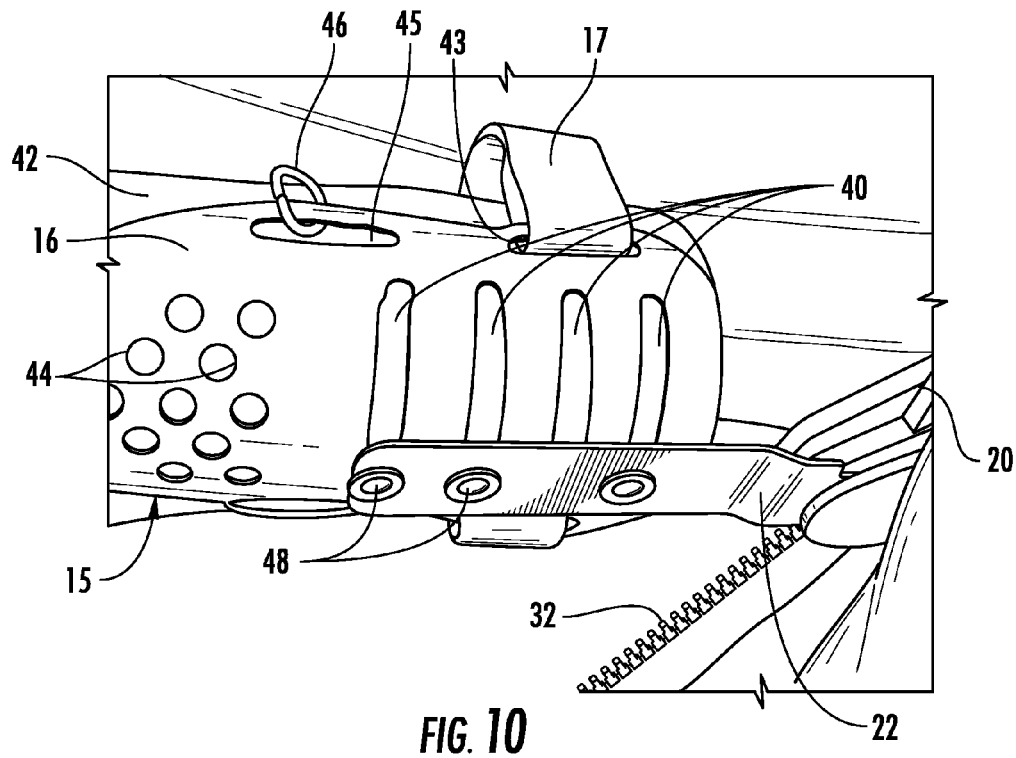
FIG. 10 is a partial perspective view of the orthosis shown in FIG. 9 in accordance with the present invention.

The concave member 16 of the WHO 15 may also include a pair of slots 43 as shown in FIGS. 10-11, for example, on each side of the concave member 16 to allow connection of the arm strap 17. For ease of illustration, only one such slot 43 is shown in FIGS. 9-11 on one side of the concave member 16. However, although not shown, a similar slot 43 may be placed on the opposite side as well to provide connection for the strap 17. Alternatively, as shown in FIG. 7, for example, strap 17 may simply wrap around the arm and WHO 15 to secure the forearm to the WHO 15.

Figure 13:
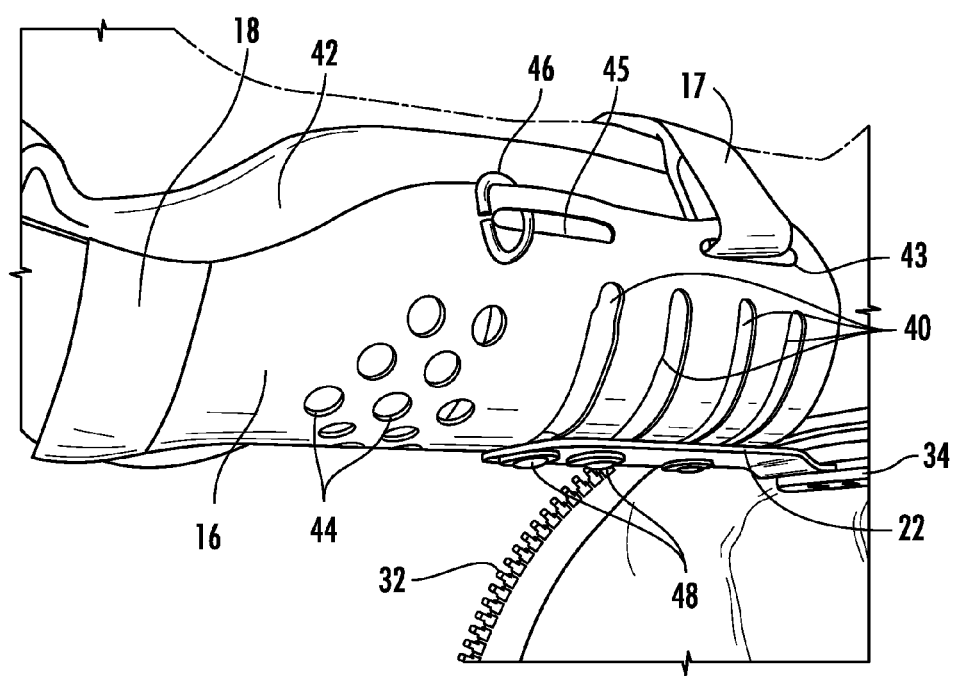
FIG. 13 is a partial perspective view of the orthosis shown in FIG. 9 in accordance with the present invention.

In one embodiment, an additional slot 45 also may be provided on the concave member 16 (preferably also on that side of the concave member 16 which is closer to the body of the user) to allow attachment of a metallic or plastic "D" ring 46 (more clearly shown in FIGS. 10 and 13). Another "D" ring 55 may be attached to a desired location on the neck strap 29 or sewn into the neck strap 29 to allow a user or therapist to connect both the "D" rings via a resistance band (e.g., rubber band 56 shown in FIG. 9) to facilitate active resistance when doing arm or shoulder exercises while maintaining the user's arm in the sling 12. In other embodiments, one or more of the "D" rings 46, 55 may be in the form of metallic or plastic hooks, cloth rings, or Velcro™ tabs.

Furthermore, the "D" ring 55 may be used at various desired points in the sling to attach resistance bands for exercises. For example, the "D" ring 55 in FIG. 9 is shown to be attached to a side of the neck strap 29 and away from the shoulder, whereas in the embodiment of FIG. 14, it is shown attached to the neck strap 29 close to the shoulder of the user. In addition to or in place of the "D" ring 55, a "D" ring or similar attachment means (not shown) may be provided on the abduction pillow 24 at an appropriate location (e.g., by insertion into a cloth tab or some other closure means provided on the pillow 24) for resistance band training in a similar manner.

FIGS. 10, 11 provide additional close-up views of the WHO 15 and its attachment to the pivotable support 20. FIG. 12 provides a top view of the pivotable support 20, the linkage of upper and lower stays 21, 22, and part of the concave member 16 of the WHO 15.

FIG. 13 illustrates another close-up perspective view of parts of the WHO 15 showing location for attaching the wrist strap 18. In one embodiment, the wrist strap 18 may include a Velcro™ surface to attach an end of the strap 18 to that surface after wrapping the strap 18 around the user's wrist or hand 30 (as shown, for example, in FIGS. 2-3). Also as shown in FIG. 13, in one embodiment, the concave member 16 of the WHO 15 may slightly curve upwards in the vicinity of the user's wrist before connecting to the ball 19 (not shown in FIG. 13, but shown in FIG. 1). Alternatively, the concave member 16 may be relatively flat in the vicinity of the user's write to keep in more of a neutral position for users. In one embodiment, the concave member 16 may have a short plastic (or metallic) extension over which the ball 19 may be mounted. In another embodiment, the ball 19 may form a part of the fabric layer 42 placed over the concave member 16. Additional details for various parts shown in FIGS. 9-13 are already provided hereinbefore and, hence, are not repeated herein for the sake of brevity.

It is noted here that the user-adjustable design of the WHO 15 according to the teachings of the present disclosure may reduce the complexity of regulating internal/external rotation of a standard sling. Furthermore, user-adjustable positions for the pillow 24 (shown and discussed below with reference to FIGS. 14-15) may also reduce the complexity of regulating degrees of abduction. The WHO 15 according to one embodiment of the present disclosure provides an orthosis that is light and stable, and which allows easy adjustments by the user to accommodate shoulder/arm movements. The WHO 15 thus may provide sufficient linear adjustment for the arm of the user to induce angular displacement of the shoulder joint to any selected position over a large clinically useful range. The WHO 15 discussed herein with reference to embodiments in FIGS. 9-13 provides an orthosis assembly 10 that is wearable while the user is ambulatory, but is also readily tolerable while the user is sitting or lying in bed. The telescoping concave member 16 of the WHO 15 may be sized and positioned to accommodate a very wide range of sizes and shapes of user forearms, thereby allowing provision of a single orthosis for the right arm and shoulder, and a single orthosis for the left arm and shoulder. The WHO 15 and its nut-and-bolt based slot engaging mechanism 48 connecting to the pivotable support 20 may allow for a variable, stable positioning of a human shoulder joint in flexion, extension, internal and external rotation, abduction and adduction, or combinations thereof, and all of these may be achieved over a large angular range and in an easy manner as discussed hereinbefore.

Figure 14:
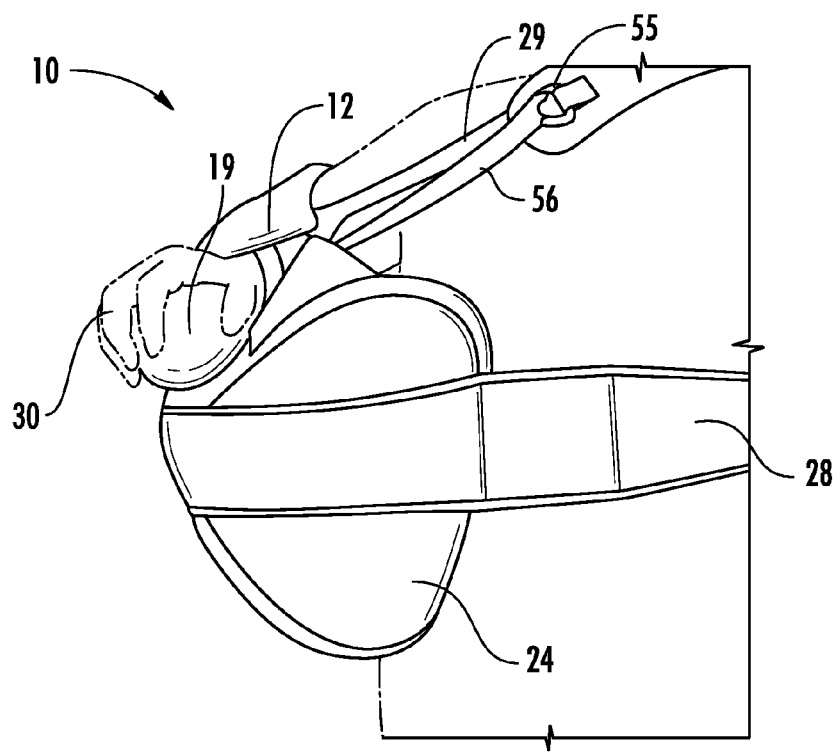
FIG. 14 is a front view of an embodiment of an orthosis as it may be employed by a user in accordance with the present invention.
Figure 15:
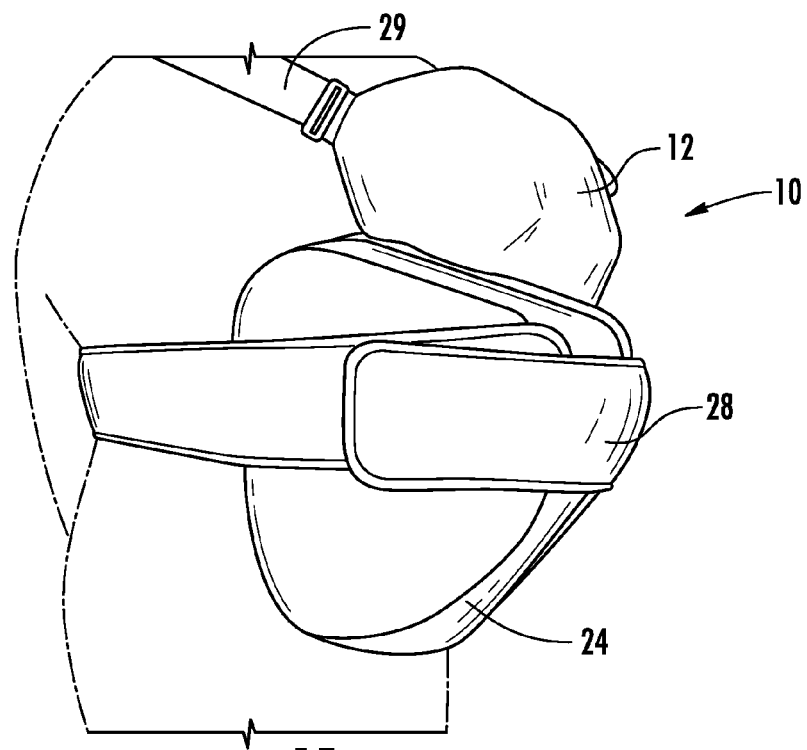
FIG. 15 is a rear view of an embodiment of an orthosis as it may be employed by a user in accordance with the present invention.

FIGS. 14 and 15 illustrate additional views of the abduction pillow 24 and its attachment to the user's waist while the user's arm is in the sling 12. As mentioned below, in one embodiment, two abduction pillows may be included (although only one such pillow 24 is shown in FIGS. 14-15) as part of the orthosis provided to the user. One of the pillows 24 may position the arm at about 90 degrees of abduction, for example, and flipping the pillow may position the arm at about 65 degrees of abduction, for example, with the orthosis assembly 10 attached. The pillow 24 may be attached to the sling 12 with Velcro™ or other suitable fastener to prevent sliding of the sling 12 (and, hence, the user's arm) when the user's arm rests on the pillow 24. The pillow 24 may be worn at waist level using the waist band 28 as illustrated in FIGS. 14-15. A second pillow may provide two angles of abduction—one side of the pillow at 40 degrees, and the other side at 25 degrees, for example. As mentioned before, in one embodiment, a single pillow (not shown) with three sides providing abduction at 90 degrees, 45, degrees, and 20 degrees, respectively, may be provided instead of two separate pillows.

As can be seen in FIGS. 16-21, an orthosis assembly 110 is provided having various parts mechanically similar to the orthosis assembly 10 shown in FIGS. 1-15 that are already discussed hereinbefore and, hence, additional discussion of those similar parts is not repeated herein for the sake of brevity. For example, but not limited to the following, padding 111 is similar to padding 11, arm strap 117 is similar to arm strap 17, wrist strap 118 is similar to wrist strap 18, grip 119 is similar to grip 19, and hand 130 is similar to hand 30. However orthosis assembly 110 provides another embodiment of an opening/closing means for another embodiment of a shoulder sling 112, another embodiment of telescoping means for a WHO 115 and various embodiments for straps 123 and pad 127 in accordance with the present invention.

Figure 16:
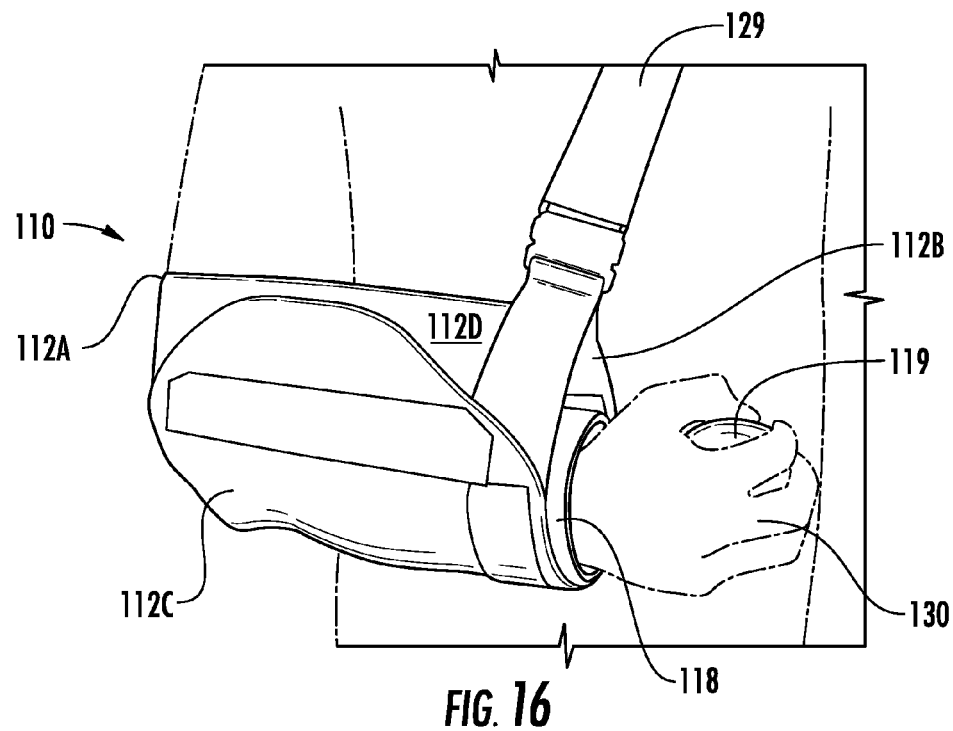
FIG. 16 is a side view of an embodiment of an orthosis as it may be employed by a user in accordance with the present invention.
Figure 17:
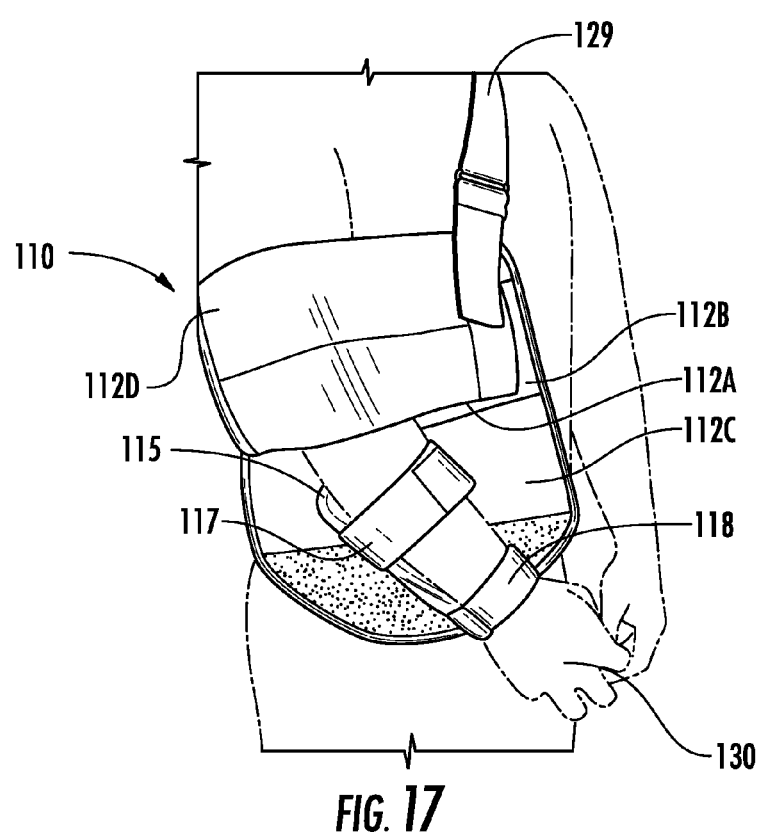
FIG. 17 is a side view of the orthosis shown in FIG. 16 in an opened orientation as it may be employed by a user repositioning their elbow in accordance with the present invention.
Figure 18:
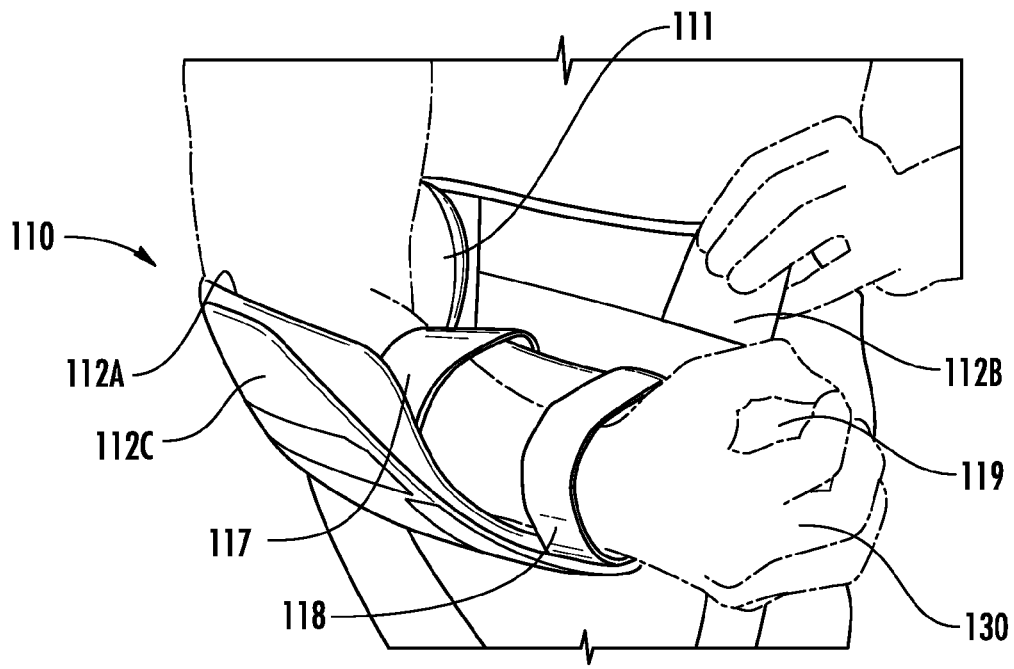
FIG. 18 is a perspective view of the orthosis shown in FIG. 16 in an opened orientation as may be employed by a user in accordance with the present invention.

FIGS. 16-18 show the shoulder sling 112 of the orthosis 110, supported by shoulder strap 129, having an outer portion 112A, an inner portion 112B, an attachment extension 112C of the inner portion 112B positioned adjacent the inner portion 112B and a securing portion 112D opposite the outer portion 112A. The shoulder sling 112 may be made of durable cloth or other materials suitable for retaining the user's arm without creating discomfort for the user due to friction with the arm of the user. Inner portion 112B may be contiguous with outer portion 112A longitudinally along the user's arm and wrap around user's arm as shown in FIG. 18. For ease of comfort and support, the area at the end of the elbow where outer portion 112A and internal inner side 112B meet may be gusseted to form somewhat of a pocket to receive the elbow and provide additional support for the user. Such gusseting may assist a user find the proper positioning the elbow in the sling 112 and may provide some limited support to the elbow while the forearm of the user may be extended out of the sling 112. Alternatively, inner and outer portions 112B, 112B may be made separately and sewn/affixed together.

Attachment extension 112C may be contiguous and/or affixed to the inner portion 112B as can be seen in FIG. 17. This attachment extension 112C may have a portion thereof that can be releasably attached to the securing portion 112D of the sling 112. Accordingly, as can be seen in FIGS. 16, 18, the attachment extension 112C may wrap under the user's arm from inner portion 112B and support the user's arm by attachment to the securing portion 112D. Securing portion 112D may be comprised of various materials that would allow attachment extension 112C to securely affix thereto including, for example, Velcro™, tacky materials, buttons, snaps, etc. Similarly, inner and outer portions 112B, 112A may be configured to open/close over the top of the user arm as shown in FIG. 18.

Figure 20:
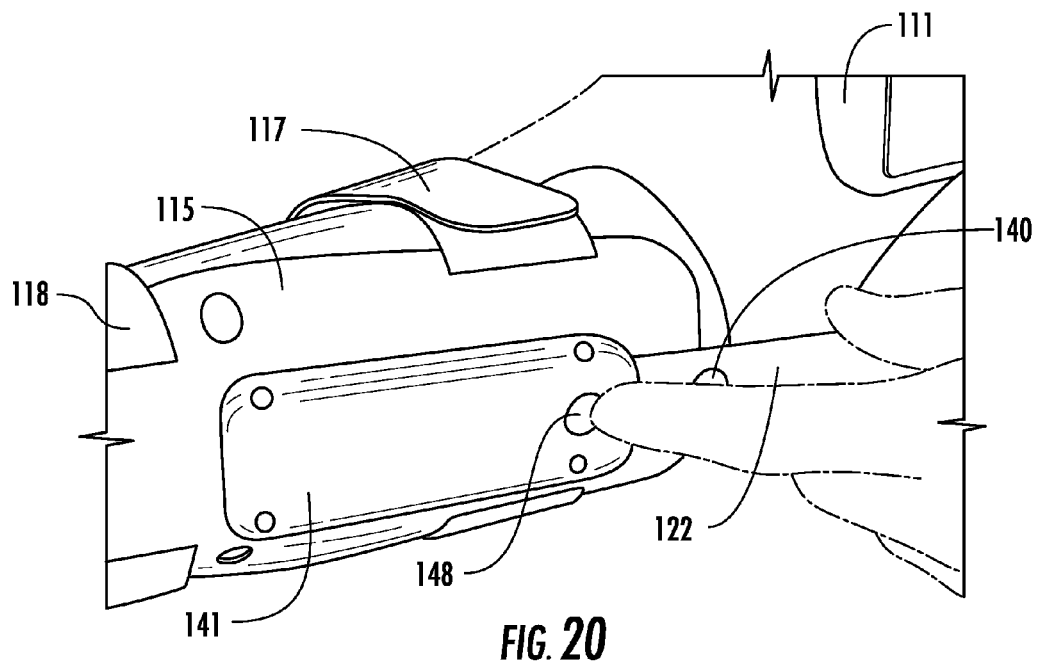
FIG. 20 is a partial perspective view of the orthosis shown in FIG. 16 as may be employed by a user in accordance with the present invention.

FIG. 20 illustrates an embodiment of the telescoping WHO 115, having an optional housing 141, apertures 140 in the lower stay 122, and an aperture engaging mechanism 148. The aperture engaging mechanism 148 may be biased to engage apertures 140 and retain the extension of the WHO 115 in a desired position. Accordingly, a user may actuate the aperture engaging mechanism 148 to disengage the aperture 140 wherein is may be engaged and translate the WHO 115 along the lower stay 122 and thus reposition the WHO 115 away from or toward the user's elbow.

Figure 19:
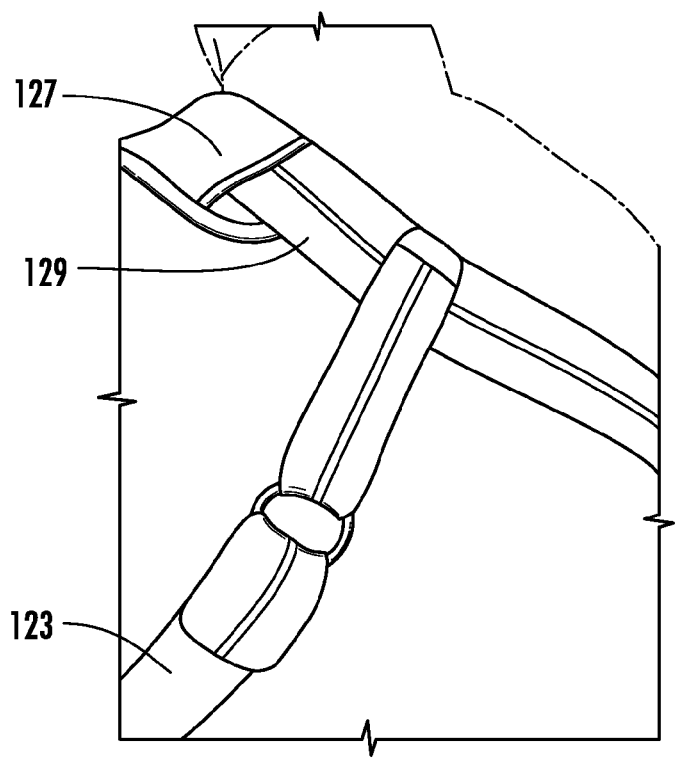
FIG. 19 is a rear view of straps of an embodiment of an orthosis in accordance with the present invention.

As can be seen in FIG. 19, the strap 112 may include a pad 127 positioned on the shoulder strap 129. The pad 127 may be repositionable and/or removable from the strap 129 so as to provide the user with various options to employ the pad 127. Further, unloader strap 123 may be employed and may be attachable to the sling 112 and shoulder strap 129. Accordingly, unloader strap 123 may provide support from the sling 112 to relieve stresses caused by the shoulder strap 129. Thus, the pad 127 and/or unloader strap 123 may increase comfort and/or assist in decreasing neck pain for the user.

Figure 21:
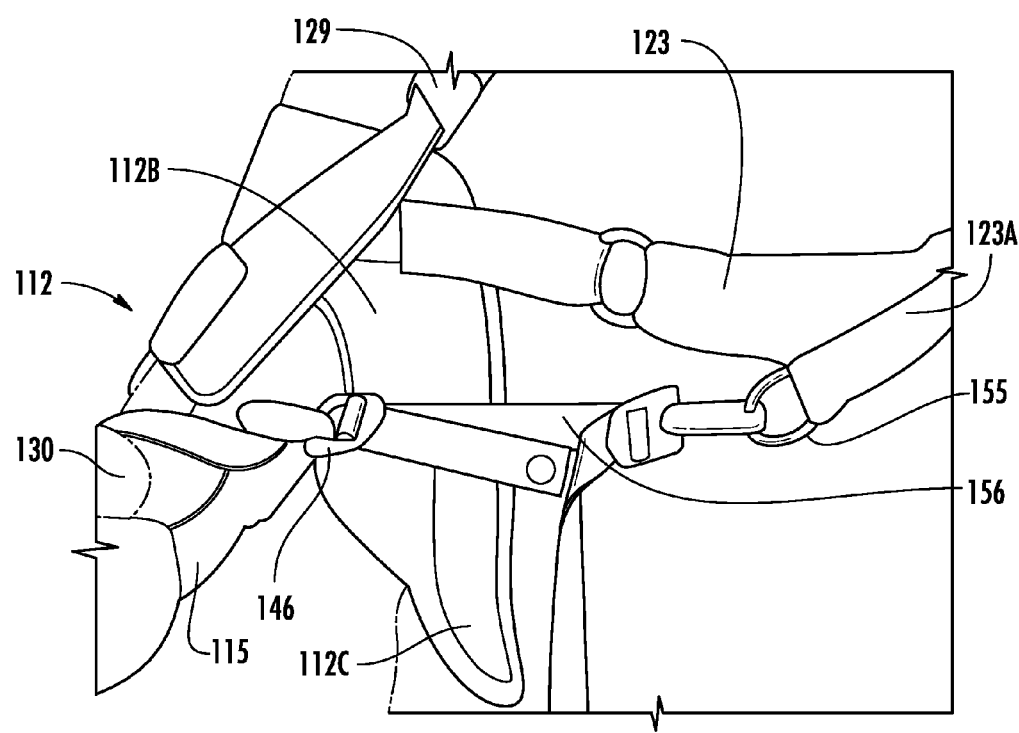
FIG. 21 is a partial perspective view of the orthosis shown in FIG. 16 in an opened orientation as may be employed by a user in accordance with the present invention.

FIG. 21 shows the attachment of the unloader strap 123 with the sling 112 at the inner portion 112B, although other attachment points may be contemplated in accordance with the present invention such as, for example, attachment to the WHO 115. Further, an auxiliary strap 123A may be supported by the unloader strap 123 for attachment of a band 156 between the sling 112 and the unloader strap 123 via D-rings 146, 155. Such attachment of the band 156 may provide resistance for the user in allowing the patient to exercise and/or perform therapy while being supported by the sling 112 and/or WHO 115.

It is noted here that, in one embodiment, various components of the orthosis assembly 10 may be provided as part of a kit. For example, such a kit may include as its components one or more of the sling 12, having its neck strap 29, the WHO 15, having one or more straps 14, 17-18, the pivotable support 20 having plastic/metal stays 21-22 (and any cloth coverings for the stays), the gel pad 38 for the pivotable support 20, any nuts and bolts to connect the WHO 15 to the pivotable support 20, one or more abduction pillows 24 and the waist band 28, the "D" rings 46, 55, and one or more resistance bands 56, etc.

The foregoing describes a shoulder and arm orthosis that addresses the need to support the shoulder and may assist in preventing cubital tunnel syndrome by allowing full flexing of the elbow without the need to remove the sling. The orthosis of the present invention promotes both stability and resistance in the physical therapy process to prevent unnecessary surgery causing additional risk and financial cost to the user and to also prevent jeopardizing of the surgeon's prior work on the shoulder surgery. Furthermore, the orthosis may be configured to provide support for the user's elbow, wrist, and hand with a pivotable support and telescoping wrist/hand orthosis (WHO).

Although the invention has been described in detail for the purpose of illustration based on what is currently considered to be the most practical and preferred embodiment(s), it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. Since other modifications and changes varied to fit particular operating requirements and environments will be apparent to those skilled in the art, the invention is not considered limited to the example chosen for purposes of disclosure, and covers all changes and modifications which do not constitute departures from the spirit and scope of this invention.

What is claimed is:

1. An orthosis assembly for supporting at least one of a shoulder, arm, wrist and hand of a user comprising:
   a sling comprising attached inner and outer portions, wherein said inner and outer portions are configured to be detached and reattached;
   a wrist/hand orthosis supported by said sling, said wrist/hand orthosis supporting a first strap configured to attach to one of the wrist and the arm of the user; and
   a second strap connected to said sling and configured to support said sling,
   wherein said wrist/hand orthosis further comprises an upper stay configured to be attached to said sling, and a lower stay in pivotal communication with said upper stay, wherein said lower stay is configured to support least one of the wrist and arm of the user.

2. The orthosis assembly of claim 1, wherein said wrist/hand orthosis further comprises a hand grip positioned at an end of said wrist/hand orthosis configured to support at least a portion of the hand of the user.

3. The orthosis assembly of claim 1, further comprising a support configured to position said sling away from the waist of the user.

4. The orthosis assembly of claim 1, wherein said inner portion further comprises an attachment extension.

5. The orthosis assembly of claim 4, wherein said outer portion further comprises a securing portion, and wherein said attachment extension is configured to be detached and reattached to said securing portion.

6. The orthosis assembly of claim 1, further comprising a zipper positioned between said inner and outer portions wherein said zipper is configured to attach and detach said inner and outer portions.

7. The orthosis assembly of claim 1, further comprising a band supported by said sling and configured to attach to said wrist/hand orthosis.

8. The orthosis assembly of claim 1, wherein said inner and outer portions form a gusset configured to receive the elbow of the user.

9. An orthosis for supporting at least one of an arm, wrist and hand of a user comprising:
 a first member configured to attach to a sling;
 a second member in pivotal communication with said first member;
 a first strap positioned about at least a portion of said second member configured to support the arm of the user;
 a second strap positioned about at least a portion of said second member near an end of said second member and configured to secure at least the wrist of the user to the second member; and
 a grip positioned at an end of said second member configured to support the hand of the user.

10. The orthosis of claim 9, further comprising a concave member attached to said second member and configured to support the arm of the user.

11. The orthosis of claim 10, further comprising apertures and an aperture engaging mechanism for securing said second member, wherein said second member is configured to allow translation of said second member with respect to said first member.

12. The orthosis of claim 10, further comprising slots and a slot engaging mechanism for securing said second member to said concave member, wherein said concave member is configured to allow translation within said slots.

13. A kit for a shoulder and arm orthosis comprising:
 a sling configured to allow opening of said sling near the bottom of said sling;
 a wrist/hand orthosis supported by said sling, said wrist/hand orthosis supporting a first strap configured to attach to one of the wrist and the arm of the user;
 a second strap connected to said sling and configured to support said sling; and
 a support configured to maintain said sling in a desired position,
 wherein said wrist/hand orthosis further comprises an upper stay configured to be attached to said sling, and a lower stay in pivotal communication with said upper stay, wherein said lower stay is configured to support at least one of the wrist and arm of the user.

14. The kit of claim 13, further comprising one or more bands configured to attach to said sling and said wrist/hand orthosis.

15. A method to control flexion or extension of the elbow joint using a pivotable support integrated in a shoulder and arm orthosis, the method comprising:
 positioning a strap of a sling of said shoulder and arm orthosis about a neck of a user;
 positioning an arm, wrist and hand of a user into a wrist/arm orthosis positioned within said sling; and
 securing the arm, wrist and hand of the user to said wrist/arm orthosis.

\* \* \* \* \*